United States Patent
Högerle

(10) Patent No.: US 12,402,896 B2
(45) Date of Patent: Sep. 2, 2025

(54) ADAPTIVE TOOL OPERATION

(71) Applicant: Aesculap AG, Tuttlingen (DE)

(72) Inventor: Roland-Alois Högerle, Tuttlingen (DE)

(73) Assignee: Aesculap AG (DE)

( * ) Notice: Subject to any disclaimer, the term of this patent is extended or adjusted under 35 U.S.C. 154(b) by 318 days.

(21) Appl. No.: 17/917,051

(22) PCT Filed: Apr. 1, 2021

(86) PCT No.: PCT/EP2021/058602
§ 371 (c)(1),
(2) Date: Oct. 5, 2022

(87) PCT Pub. No.: WO2021/204664
PCT Pub. Date: Oct. 14, 2021

(65) Prior Publication Data
US 2023/0149026 A1 May 18, 2023

(30) Foreign Application Priority Data

Apr. 9, 2020 (DE) .......................... 102020109932.0

(51) Int. Cl.
*A61B 17/16* (2006.01)
*A61B 17/00* (2006.01)

(52) U.S. Cl.
CPC ...... *A61B 17/1626* (2013.01); *A61B 17/1628* (2013.01); *A61B 2017/00039* (2013.01); *A61B 2017/1602* (2013.01)

(58) Field of Classification Search
CPC ................ A61B 17/16; A61B 17/1613; A61B 17/1615; A61B 17/1617; A61B 17/162;
(Continued)

(56) References Cited

U.S. PATENT DOCUMENTS

| | | | |
|---|---|---|---|
| 5,538,423 A * | 7/1996 | Coss | A61C 1/0015 433/101 |
| 6,616,446 B1* | 9/2003 | Schmid | A61B 17/8875 433/224 |
| 7,362,062 B2* | 4/2008 | Schneider | H02P 6/182 318/609 |

(Continued)

FOREIGN PATENT DOCUMENTS

| DE | 20110944 U1 | 10/2001 |
|---|---|---|
| DE | 202004004700 U1 | 6/2004 |

(Continued)

OTHER PUBLICATIONS

English Translation of the Written Opinion for International Application No. PCT/EP2021/058602, mailed Jul. 6, 2021, 7 pages.

(Continued)

*Primary Examiner* — Eric S Gibson
(74) *Attorney, Agent, or Firm* — Buchanan Ingersoll & Rooney PC

(57) ABSTRACT

A medical apparatus having a control device, the control device being designed to store a target current demand in accordance with requirements of a drive of the medical apparatus, and to determine a minimum current demand corresponding to a minimum requirement of the drive of the medical apparatus during a current operation and, based on the minimum current demand, to adapt a maximum value of the target current demand for the current operation of the medical apparatus, said maximum value being provided to limit the current.

14 Claims, 3 Drawing Sheets

(58) Field of Classification Search
CPC ............ A61B 17/1622; A61B 17/1624; A61B 17/1626; A61B 17/1628; A61B 17/1655; A61B 17/1657; A61B 17/1659; A61B 17/1662–1693; A61B 17/1695; A61B 2017/1602; A61B 2090/064; A61B 2090/066; A61C 1/0007; A61C 1/0015; A61C 1/003; A61C 2204/007

See application file for complete search history.

(56) References Cited

U.S. PATENT DOCUMENTS

| | | | | |
|---|---|---|---|---|
| 2002/0087179 | A1* | 7/2002 | Culp | A61B 17/1626 606/1 |
| 2015/0377969 | A1* | 12/2015 | Muto | A61C 1/003 433/131 |
| 2023/0149026 | A1* | 5/2023 | Högerle | A61C 1/003 606/84 |

FOREIGN PATENT DOCUMENTS

| | | | | |
|---|---|---|---|---|
| DE | 102004038415 | A1 | | 3/2006 |
| DE | 102018130376 | A1 | | 6/2020 |
| DE | 102020109932 | A1 * | 10/2021 | ......... A61B 17/1626 |
| EP | 0890343 | A2 | | 1/1999 |
| EP | 4081137 | B1 * | 5/2023 | ......... A61B 17/1626 |
| ES | 2951492 | T3 * | 10/2023 | ......... A61B 17/1626 |
| JP | 2002514464 | A | | 5/2002 |
| JP | 2007195993 | A | | 8/2007 |
| JP | 2016007366 | A | | 1/2016 |
| WO | WO-9952456 | A1 * | 10/1999 | ..... A61B 17/320758 |
| WO | 2018194909 | A1 | | 10/2018 |
| WO | WO-2021204664 | A1 * | 10/2021 | ......... A61B 17/1626 |

OTHER PUBLICATIONS

German Search Report for German Application No. 10 2020 109 932.0.0, with partial translation, dated Nov. 25, 2020, 6 pages.
International Search Report and Written Opinion for International Application No. PCT/EP2021/058602, dated Jul. 6, 2021, 10 pages.
Japanese Notice of Reasons for Refusal for Japanese Application No. 2022-561508, dated Apr. 5, 2023 with translation, 5 pages.
Office Action (Notice of Reasons for Refusal) issued Jul. 8, 2025, by the Japanese Patent Office in corresponding Japanese Patent Application No. 2022-561508 and an English translation of the Office Action. (9 pages).

* cited by examiner

ADAPTIVE TOOL OPERATION

This application is a U.S. National Phase application of PCT International Application No. PCT/EP2021/058602, filed Apr. 1, 2021, which claims the benefit of 102020109932.0, filed Apr. 9, 2022, both of which are incorporated by reference herein.

The invention relates to a medical device, in particular a surgical motor system and a method of operating a medical device.

BACKGROUND

The background of the invention is to provide automated and controlled operation of a medical device. This includes surgical motor systems, such as handpieces and hand milling devices. In some instances, the surgical motor systems have a handpiece and a spacer sleeve attachable or attached thereto, which allows greater distances to be covered without having to move the device closer to the patient. In the course of use, the device suffers from wear, which can have several origins. This includes lubricant wear and wear of the elements contained in a drive train of the surgical motor system.

There may be a need to provide concepts that take into account the wear of the medical device.

BRIEF DESCRIPTION OF THE INVENTION

Thus, it is the object of the invention to provide a medical device and an associated method that provide safe and controlled operation even under wear.

According to the invention, this object is solved by providing a medical device, in particular a surgical motor system. The medical device has a control device. The control device is configured to store a target current demand according to requirements of a drive of the medical device. The control device is furthermore configured to determine a minimum current demand according to a minimum requirement of the drive of the medical device during a current operation. Furthermore, the control device is configured to adjust, based on the minimum current demand, a maximum value of the target current demand provided to limit the current for the current operation of the medical device.

In this way, safe and controlled operation under wear can be provided.

The requirements mentioned herein may be requirements in the sense of torque requirements. Here, a torque can be requested from the drive of the medical device via a foot pedal of the medical device. The torque requirement may be directly proportional to the current demand. The current demand may be a total current demand of the medical device that is consumed when connected to a power supply during use. Here, the current demand can be adapted to a load in terms of a torque requirement and material to be processed, for example bone.

The control device may be configured to continuously measure or respectively determine the minimum current demand during the current operation. The control device can be configured to adapt the maximum value of the target current demand in case the minimum current demand changes.

Thus, the maximum value can be adapted adaptively.

The control device may be located within a handpiece of the medical device. For example, in a grip piece provided for this purpose, which is configured to be grasped by a user.

The minimum current demand may correspond to a no-load operation of the medical device during the current operation. Thus, a minimum value of the target current demand may also correspond to a no-load operation of the medical device during a first operation or during a first start-up or a first series of measurements of the medical device.

In other words, the minimum value of the target current demand may correspond to the no-load operation of the medical device in time before the current operation.

Thus, different time series can be compared and a maximum current demand can be adjusted in terms of a maximum torque demand.

The current operation may be an operation after one or more times of use of the medical device. The current operation may correspond to a current use, for example, during use and active power supply of the medical device.

The target current demand may be associated with a dedicated combination of torque-effecting elements of a drive train of the medical device, for example motor/gear/shaft/ball bearing/tool. This combination can define the target current demand. The target current demand can be or can be represented in the form of a curve, for example a course of the curve.

This allows an adapted current demand to be set or to be specified for each type of use.

The stored target current demand can be stored as data in a memory of the control device. The control device may have a separate memory for this purpose outside the medical device or the handpiece. Likewise, the memory may be present within the medical device or the handpiece. The memory may also be part of an integrated control device in the form of a printed circuit board. The memory may be provided in the form of an EEPROM and may simply be housed in the handpiece.

The control device may be configured, when the minimum current demand exceeds a threshold value, to trigger a signal containing information about wear of the medical device, which is intended for a user of the medical device. The signal may be passed to or written into a display device or a memory, respectively. This allows the information of the signal to be either passed to the user or to be logged in the memory for further use.

According to the invention, the object defined above is also solved by providing a method for operating a medical device, preferably as described above. The method comprises storing, by a control device of the medical device, of a target current demand according to requirements of a drive of the medical device. The method further comprises determining, by the control device, of a minimum current demand corresponding to a minimum requirement of the drive of the medical device during a current operation. The method further comprises adjusting, by the control device, based on the minimum current demand, of a maximum value provided for limiting the current of the target current demand for the current operation of the medical device.

Thus, safe and controlled operation under wear can be provided.

The target current demand may correspond to an ex-factory condition of the medical device. The stored target current demand may have been measured or determined during initial operation of the medical device.

That is, the medical device is equipped with a control device that contains or has stored data regarding the target current demand. Hereby, the medical device can be delivered to a customer who is equipped with a controlled medical device. The data can furthermore be collected. For this purpose, a server may be provided that stores information about current demand and target current demand. This data may be provided along with user-supplied wear information, from which conclusions can be drawn about the use and condition of the medical device.

In other words, the invention relates to the determination of relevant data and data provision, for example of an artificial intelligence, for the safe and automatically controlled operation of tools and drives. In this regard, data generation may be performed without additional sensors, based solely on existing data in the control device regarding engine operation.

In one or more embodiments, a total drive current may be measured/determined or stored along time. The methodology for this may be provided as follows.

First, a determination of the total drive current course 'reference curve' (in particular under laboratory conditions) can be carried out. Each individual combination (motor/gearbox/tool) in ideal new condition with optimal tribology (oil type/oil quantity) up to the load of the respective tool for maximum stock removal without tool overload can be considered for this.

After that, the maximum total drive current (Imax opt=Mmaxopt: maximum value of the total drive current curve=limit of the current, this value corresponds to the maximum permissible torque at the cutting edge of the respective tool) can be specified.

After this, a limit of the total drive current (at Imax opt) can be specified. Thus, a limit of the maximum torque at a tool cutting edge for the individual combination can be specified by the control device. This torque limitation of the respective tools is only correct (with this method) when operating with ideal drives (new, ideal lubrication).

For example, with increasing wear of the motor and of the gearbox as well as unsuitable lubrication quantity/lubricant, an individual correction value (Icor) has to be added to the maximum total drive current (Imax opt). The increasing wear as well as unsuitable lubrication increase the operating torques of the system and reduce the torque at the tool cutting edge.

Furthermore, a methodology for determining the wear correction value may be provided. The minima of the total drive current curve (Isys) can correspond to the current demand (torque demand) of the total drive system without bone contact (cutter runs at the respective speed (given by e.g. a pedal position providing the torque demand and coupled to the medical device) without contact to the bone, torque at the cutting edge=0 Nm).

The minima of the total drive current curve (Isysist) can be determined during the entire operation. An increase in the minimum values (Isysist) compared to the reference curve (Isysopt) can be a measure of the wear and lubrication condition of the drive system. The difference between the respective minimum value measurement (Isysist) and the reference minimum value (Isysopt) is added to the limit of the current=maximum value of the total drive current curve (Imaxist(t)=Imaxopt(t)+Icor(t)).

If, in addition, the difference between the minimum currently measured or determined in the process exceeds a predefined value (Icormax), the permissible wear level has been reached. This can then be documented and incorporated into the further flow of information (predictive maintenance).

Further information can also be obtained from the continuous measurement of the no-load current (Isysist) and can be used to provide data for artificial intelligence.

For example, the course of the no-load current (Isysist) can be almost constant only in an optimal system (new condition, lubrication).

As another example, in new systems that are 'over-oiled', the value of an excessively high no-load current (Isysist) may decrease during operation.

Furthermore, for an inadequately oiled system, the no-load current (Isysist) may increase significantly over the course of the operation.

Likewise, the current increase in the no-load current (Isysist) can be used to draw conclusions about the type and shape of the tool.

Finally, further knowledge and correlations may be assumed as experience of this measurement technique increases.

It is clear to the person skilled in the art that the explanations set forth herein may be/are implemented using hardware circuits, software means, or a combination thereof. The software means may be related to programmed microprocessors or a general computer, an ASIC (Application Specific Integrated Circuit) and/or DSPs (Digital Signal Processors).

For example, the medical device, in particular the control device, may be partially implemented as a computer, a logic circuit, an FPGA (Field Programmable Gate Array), a processor (for example comprising a microprocessor, a microcontroller (µC) or a vector processor)/core (main memory, may be integrated in the processor or used by the processor)/CPU (central processing unit; wherein multiple processor cores are possible), an FPU (floating point unit), an NPU (Numeric Processing Unit), an ALU (Arithmetic Logical Unit), a coprocessor (additional microprocessor to support a main processor (CPU)), a GPGPU (General Purpose Computation on Graphics Processing Unit), a parallel computer (for simultaneous execution of computational operations on several main processors and/or graphics processors, among others) or a DSP.

It is clear to the person skilled in the art that even if the details described herein are described with respect to a method, these details may also be realized in a suitable device, a computer processor or a memory connected to a processor, wherein the memory is provided with one or more programs that perform the method when executed by the processor. Here, methods such as swapping and paging can be used.

Although some of the aspects described above are described with respect to the medical device, these aspects may also apply to the method. Likewise, the aspects described above with respect to the method may apply to the device in a corresponding manner.

If it is said in the present case that a component is 'connected' to another component, 'is in connection' with it or 'accesses it', this can mean that it is directly connected to it or directly accesses it; it should be noted here, however, that a further component may lie in between. On the other hand, if it is said that a component is 'directly connected' to or 'directly accesses' another component, this is to be understood to mean that there are no other components in between.

BRIEF DESCRIPTION OF THE FIGURES

The invention is explained below with the aid of drawings. The following is shown.

The figures are merely schematic in nature and serve solely to aid understanding of the invention. Identical elements are provided with the same reference signs. The features of the individual embodiments can be interchanged.

In addition, spatially relative terms, such as 'located below,' 'below,' 'lower,' 'located above,' 'upper,' 'on the left,' 'left,' 'on the right,' 'right,' and the like, may be used herein to simply describe the relationship of an element or structure to one or more other elements or structures shown in the figures. The spatially relative terms are intended to include other orientations of the component in use or in operation in addition to the orientation shown in the figures. The component may be oriented differently (rotated 90 degrees or in a different orientation), and the spatially relative descriptors used herein may likewise be interpreted accordingly.

FIGURE DESCRIPTION

The medical device and the method will now be described using embodiments. In the following, this will be done by means of graphs.

Figure 1:
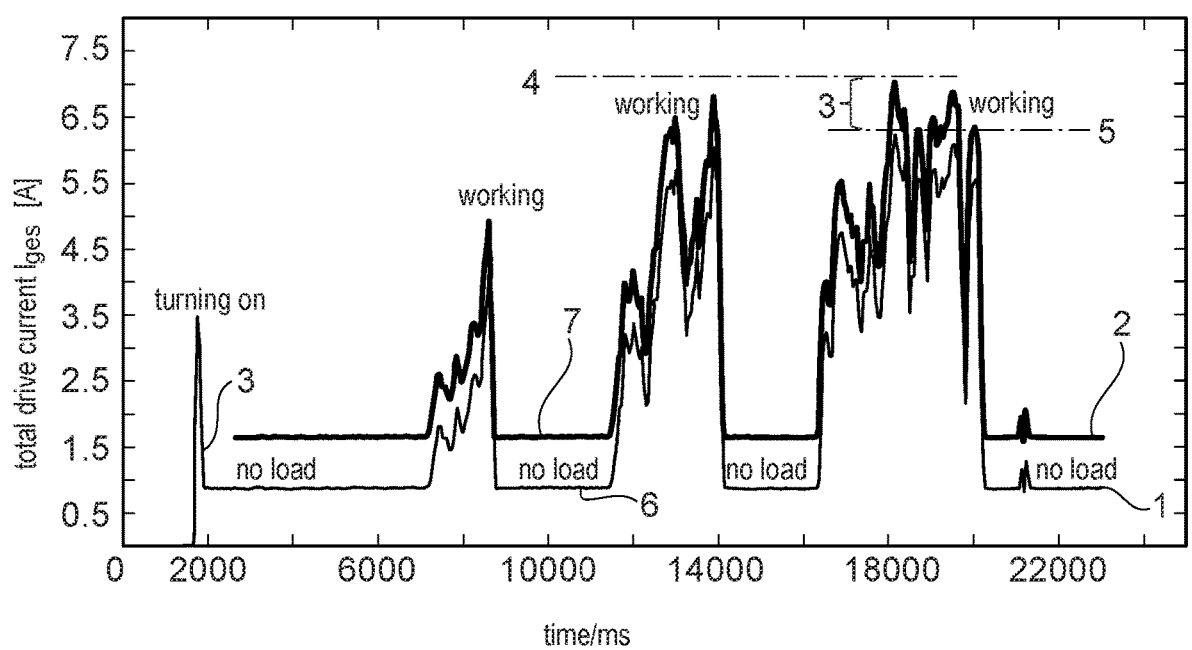
FIG. 1 shows a schematic representation of a currently active drive current and a reference current curve.

FIG. 1 shows a schematic representation of a currently active drive current and a reference current curve corresponding to the drive current of an optimal medical device. The optimal medical device is to be understood in such a way that wear of the elements of the medical device is minimized and an optimal lubrication of the drive train of the medical device is present.

FIG. 1 shows two courses of curves, one denoting a target current demand in the sense of a reference curve 1 and the other one denoting a currently active current demand 2, which is present during an assumed current operation of the medical device as described herein. The ordinate shows the total drive current in amperes and the abscissa shows the time in milliseconds.

In the following, reference curve 1 will be discussed. From left to right, the individual changes in the curve can be seen in such a way that at a switch-on time, the current rises like a peak and then falls again until it reaches a no-load current that is just below 1 A. Further to the right, the medical device enters a work mode, causing the current demand to increase. After completion of the work step, the current curve transitions to the no-load state. The no-load state denotes in particular the minimum target current demand 6. After the no-load state, the medical device switches to a work mode if required, which is higher than the first work mode, and thus the target current curve (reference curve) 1 rises again. Due to the different requirements during the work step, the target current curve 1 does not run linear but only has a tendency to corresponding to increasing total drive current. After completion of the work step, the medical device returns to the no-load state, i.e. the minimum target current demand 6. This is followed by another work step which, as the current curve shows, is more intensive and longer and thus requires a higher target current demand. It reaches a maximum of 5, which corresponds to the maximum target current demand 5. After completion of the work and with further connection to a power supply, the medical device goes back into no-load operation and thus only requires the minimum target current demand 6.

Compared to the reference curve 1, the currently active current demand 2 is shifted here by a step, namely a correction value 3 in the ordinate direction. This results in an upward shift of the curve as shown in FIG. 1. The maximum currently active current demand set in this way is thus increased to the maximum current demand 4, which differs from the maximum target current demand 5 by the correction value 3. The correction value 3 results from the difference of the no-load modes in the currently active state compared to the optimum state according to the target current demand curve 1. Here, the minimum currently active current demand 7 and the minimum target current demand 6 are compared with each other or, respectively, only a difference is formed which is added to the maximum target current demand 5. This results in the maximum currently active current demand 4. Furthermore, it should be noted that the respective work steps are the same here, except that the currently active current demand curve 2 is a medical device that is already in use.

Further details and aspects are mentioned in connection with the embodiments described above or below. The embodiment shown in FIG. 1 may have one or more optional additional features corresponding to one or more aspects mentioned in connection with the proposed concept or embodiments described below with respect to FIG. 2.

Figure 2:
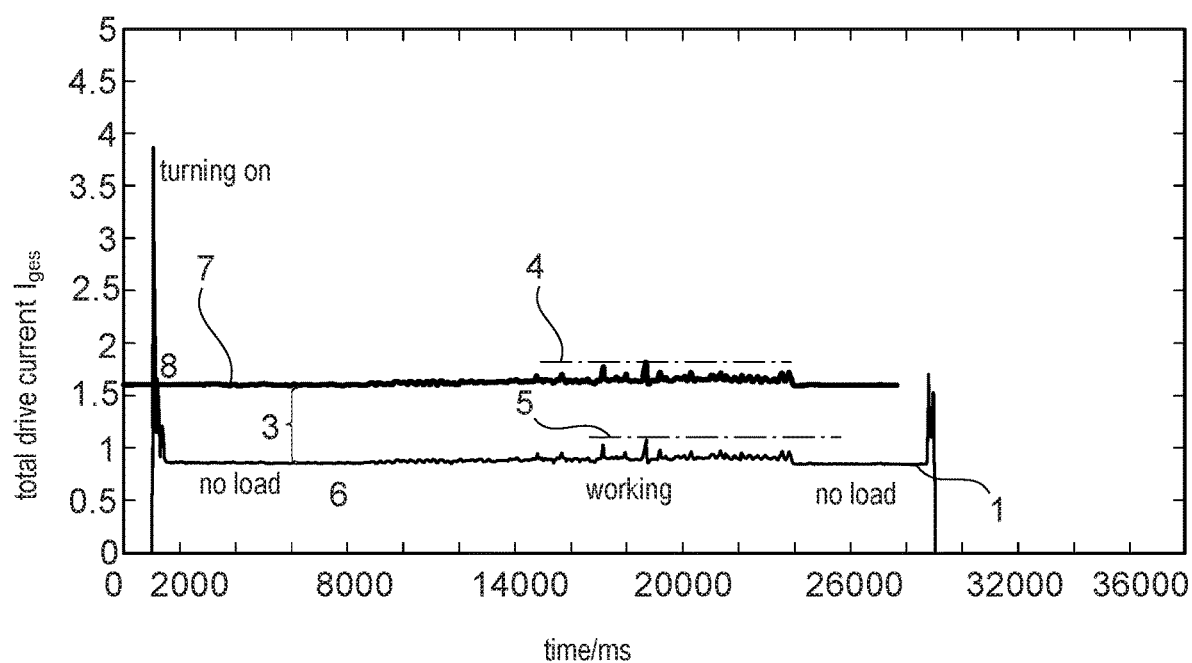
FIG. 2 shows a schematic representation of a currently active drive current and a reference current curve.

FIG. 2 shows a schematic representation of a currently active drive current and a reference current curve according to a drive current. The difference between FIG. 1 and FIG. 2 is that in FIG. 1, a cutter with a larger diameter, namely 6 mm, was used, whereas in FIG. 2 a cutter with a smaller diameter, namely 1 mm, was used. The main difference in the observation of FIGS. 1 and 2 lies in the tendency of the current curves, whereas in FIG. 1 strong increases are shown, less strong increases are present in FIG. 2.

Also shown in FIG. 2 is the total drive current over time in ms. In a power-on condition of the medical device, the current increases strongly, almost up to 4 A. Then the current drops again to a minimum target current demand, according to a no-load condition of the medical device. After the no-load mode, the work mode begins, shown by the ripples in the course of the curve. The ripples comprise a maximum target current demand 5, whereas the course of the curve in the no-load operation comprises a minimum target current demand. This allows a limit of the current to be set during operation according to the maximum target current demand. After the end of the work mode, the medical device returns to the no-load mode and assumes the minimum target current demand 6. This procedure corresponds to the procedure in FIG. 1. It can also be seen that the maximum currently active current demand 4 is covered via the correction value 3 and not the maximum target current demand. The maximum current demand 4 is therefore the result of adding the correction value 3 and the maximum target current demand 5.

In comparison to FIG. 1, FIG. 2 also shows a correction value maximum 8, which is intended to form a limit for the correction value 3. If the correction value 3 exceeds a threshold value, which is given by the correction value maximum 8, different events can take place. These events may be forwarding of a message to a superordinate instance or the communication of this information to a user. This can be used to determine that there is too much wear or over-oiling or under-oiling of the medical device or elements thereof.

Figure 3:
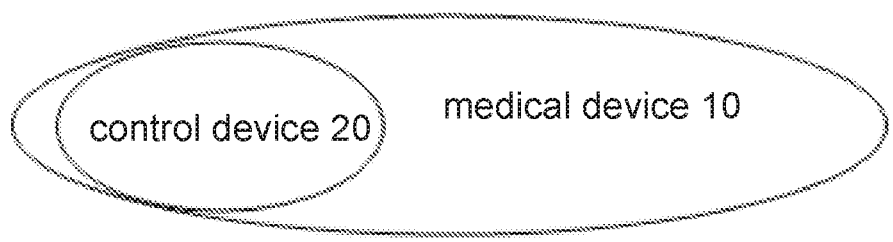
FIG. 3 schematically illustrates an example of a medical device with a control device.

FIG. 3 shows an example of a medical device 10 with a control device 20 that may be located within the medical device or outside/partially outside the medical device.

LIST OF REFERENCE SIGNS 1 target current demand (reference curve);
2 currently active current demand;

3 correction value (Icor);
4 maximum currently active current demand (Imaxist);
5 maximum target current demand (Imaxopt);
6 minimum target current demand (Isysopt);
7 minimum currently active current demand (Isysist);
8 correction value maximum (Icor);
10 medical device;
20 control device.

The invention claimed is:

1. A medical device comprising:
   a drive;
   a control device configured to store a target current demand according to requirements of the drive, and to determine a minimum current demand according to a minimum requirement of the drive during a current operation and, based on the minimum current demand, to adjust a maximum value of the target current demand provided to limit the current for the current operation of the medical device; and
   wherein the control device is configured, when the minimum current demand exceeds a threshold value, to trigger a signal containing information about wear of the medical device, which is intended for a user of the medical device.

2. The medical device according to claim 1, wherein the control device is configured to continuously measure the minimum current demand during the current operation and to adapt the maximum value of the target current demand accordingly in case the minimum current demand changes.

3. The medical device according to claim 2, wherein the minimum current demand corresponds to a no-load operation of the medical device during the current operation.

4. The medical device according to claim 2, wherein a minimum value of the target current demand corresponds to a no-load operation of the medical device in time before the current operation.

5. The medical device according to claim 2, wherein the current operation is an operation after one or more times of use of the medical device.

6. The medical device according to claim 2, wherein the target current demand is associated with a dedicated combination of torque-effecting elements of a drive train of the medical device.

7. The medical device according to claim 2, wherein the stored target current demand is stored as data in a memory of the control device.

8. The medical device according to claim 1, wherein the minimum current demand corresponds to a no-load operation of the medical device during the current operation.

9. The medical device according to claim 1, wherein a minimum value of the target current demand corresponds to a no-load operation of the medical device in time before the current operation.

10. The medical device according to claim 1, wherein the current operation is an operation after one or more times of use of the medical device.

11. The medical device according to claim 1, wherein the target current demand is associated with a dedicated combination of torque-effecting elements of a drive train of the medical device.

12. The medical device according to claim 1, wherein the stored target current demand is stored as data in a memory of the control device.

13. A method for operating a medical device, wherein the method comprises:
    storing, by a control device of the medical device, of a target current demand according to requirements of a drive of the medical device;
    determining, by the control device, of a minimum current demand corresponding to a minimum requirement of the drive of the medical device during a current operation; and
    adjusting, by the control device, based on the minimum current demand, of a maximum value provided for limiting the current of the target current demand for the current operation of the medical device; and
    triggering, by the control device, a signal containing information about wear of the medical device, which is intended for a user of the medical device, when the minimum current demand exceeds a threshold value.

14. The method according to claim 13, wherein the target current demand corresponds to an ex-factory condition of the medical device or, respectively, the stored target current demand is measured during initial operation of the medical device.

* * * * *